United States Patent [19]

Tagg

[11] Patent Number: 4,657,026
[45] Date of Patent: Apr. 14, 1987

[54] APNEA ALARM SYSTEMS

[76] Inventor: James R. Tagg, 510 Hays Ave., Pittsburgh, Pa. 15210

[21] Appl. No.: 885,176

[22] Filed: Jul. 14, 1986

[51] Int. Cl.⁴ ............................................. A61B 5/08
[52] U.S. Cl. ................................. 128/721; 128/782
[58] Field of Search ............... 128/714, 721, 774, 782, 128/722, 723, 663; 33/1 PT, DIG. 13; 340/665, 666

[56] References Cited

U.S. PATENT DOCUMENTS

| | | | |
|---|---|---|---|
| 3,760,794 | 9/1973 | Basham | 340/665 |
| 4,064,869 | 12/1977 | Defares et al. | 128/721 |
| 4,169,462 | 10/1979 | Strube | 128/721 |
| 4,258,720 | 3/1981 | Flowers | 128/774 |
| 4,492,279 | 1/1985 | Speckhast | 128/721 |
| 4,576,179 | 3/1986 | Manes et al. | 128/721 |

*Primary Examiner*—Kyle L. Howell
*Assistant Examiner*—Max F. Hinderburg
*Attorney, Agent, or Firm*—Buell, Ziesenheim, Beck & Alstadt

[57] ABSTRACT

An apnea alarm apparatus detects the cessation of breathing of a human by monitoring movement of the ribcage by sensor means. The sensor means are connected to a summing amplifier which provides an electrical signal indicative of the breathing movement of the ribcage and upon a change in successive electrical signals, which indicates apnea, an alarm is activated.

5 Claims, 7 Drawing Figures

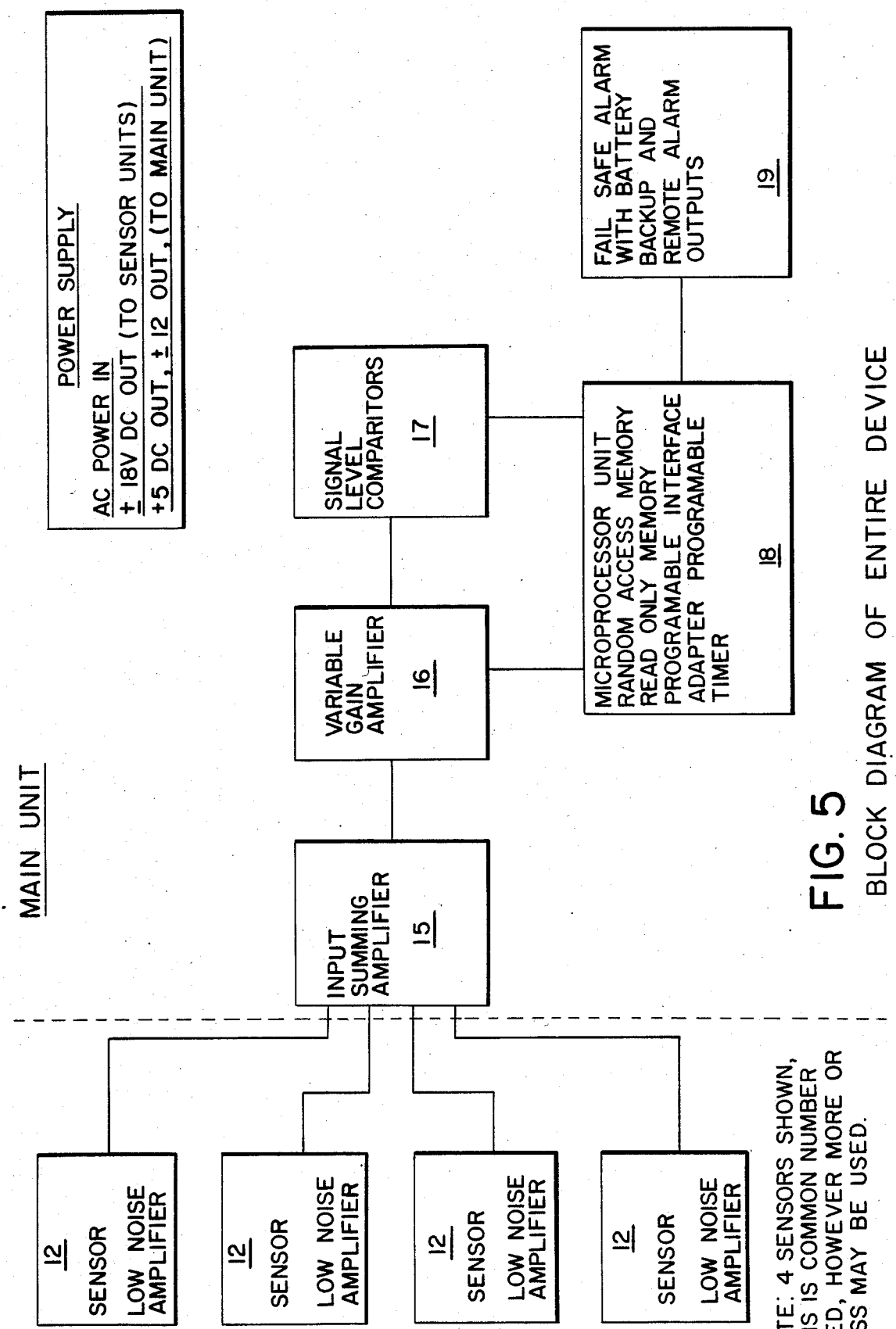
FIG. 5  BLOCK DIAGRAM OF ENTIRE DEVICE

APNEA ALARM SYSTEMS

This invention relates to apnea alarm systems and particularly to a system for continuously monitoring certain critical body functions of an infant and sounding an alarm if one or more of those functions ceases or becomes abnormal.

Death from apnea, frequently called "crib death" or "cot death", is an all too frequent occurrence, particularly in premature infants. Such deaths occur from the cessation of breathing by the infant. Death is not immediate upon cessation of breathing and the child can be revived and breathing induced by proper stimuli and other means if given in time. This, of course, requires prompt detection and swift action thereafter. The general nature of the problem has long been recognized and many attempts at a solution have been proposed over the years.

Lewis U.S. Pat. No. 3,631,438, provides a mattress, a sensory alarm and a switch for operating the alarm in the absence of compression of the mattress after a preset time period from a previously detected compression. The system requires a compartmentalized air mattress with air connecting means between the compartments to a central duct or chamber having an anemometer in the center, including a thermistor and leads to an alarm system. This is a very complex system requiring a special mattress and central air system.

Sielaff U.S. Pat. No. 3,727,606 provides another form of apnea detector involving again a fluid tight mattress with a connection to a fluid pressure sensitive transducer which in turn signals a read out signal device. A pop-off valve is provided for bypassing large air changes caused by gross body movements. Here again, a special mattress is required. If for any reason the mattress develops even a pin hole leak it will become inoperative.

Lawson U.S. Pat. No. 4,146,885, like Lewis provides an apnea detector involving an anemometer and detection system connected to a closed cell beneath the infant supported on a resilient diaphragm. Here again, a special bed and air cell structure is involved which is expensive and limited in use.

Strube U.S. Pat. No. 4,169,462 discloses an apnea detector designed to be attached directly to the child to detect body movements. This form of device is complex and uncomfortable to a child and likely to be disconnected and produce false alarms by the child's normal movements.

Other more recent attempts to solve this problem appear in Frost U.S. Pat. No. 4,245,651 and Friesen et al. U.S. Pat. No. 4,438,771 both of which relate to pad devices which are designed to warn of cessation of breathing.

All of these devices are basically usable only in a hospital type environment where their expense can be justified by continual use and where personnnel are available for maintenance and constant supervision. Such devices are not of the type or construction suitable for use in the home where most apnea deaths occur and where the transient motion of people moving about, of weather and wind changes, opening and closing of doors and windows, heating and air condition equipment can play havoc with such prior art devices.

I have invented an apnea detector which provides a high rejection of noise caused by the normal atmospheric changes in air pressure which affect detectors of the air pressure type. My detector eliminates the danger of strangulation, tape rash, discomfort, electrocution, false alarms, etc. which occur with devices attached to the child.

I provide an apparatus for detecting the cessation of breathing of a human in a crib or bed having a frame for support. The apparatus includes a sensor means on the frame of the crib or bed which converts each change in vertical force on said frame to an electrical output signal. A summing amplifier receiving the electrical output signals from all sensors on the frame provides an output summed signal. A variable gain means in the summing amplifier provides matching of the summed signal with the physical parameters of the patient, microprocessor means comparing successive said signals and providing an output signal if a change occurs and at least one of audible and physical output alarm means receiving the signal from the microprocessor. Preferably the sensor means is a piezo electric or strain gauge transducer coupled to an amplifier to produce an electrical output signal. The alarm means is preferably a buzzer combined with a flashing light as the physical output alarm. Preferably, the crib or bed is provided with a standard foam mat upon which the human rests.

In operation the sensing of the breathing through the foam mat is possible because when, for example, an infant lies on the mat and breathes, the uppermost side of the infant's ribcage moves up and down as the infant inhales and exhales. Since the upper portion of the ribcage has mass, the moving of this mass in an up and down motion is an acceleration of a mass, and a force equal and opposite is exerted against the mat by the infant's body, in particular that side of the rib cage in contact with the foam mat. The mat in turn transmits the instantaneous sum of the infant's body weight and the force from the acceleration of the ribcage mass during breathing to the frame of the crib or bed and finally to the sensors.

Due to the wide range of signal strength from the sensors resulting from a wide range of possible patient weights and wide range of breathing rates, it is necessary for the gain of the amplifier after the summing of the signals to be variable so that the signal can be amplified more when low, such as when monitoring a light weight patient or one with a slow breathing rate. On the other hand, the signal can be amplified less when monitoring a relatively heavy patient or one with a fast breathing rate. This matching of the gain of amplification of the signal to the patient will provide a usable signal for decoding and analyzing the breathing rate of the patient throughout the range of patient weight and breathing rate.

The units can be chained together when used in a nursery to connect to one alarm at a main nurse's desk along with an alarm light and audible alarm at each bed unit acting independently to signal the unit that triggers the alarm.

In the foregoing general description I have set out certain purposes and advantages of my invention. Other objects, purposes and advantages of the invention will be apparent from a consideration of the following description and the accompanying drawings in which:

FIG. 5 is a block diagram of the entire device showing the sensor(s), input and variable gain amplifiers, microcomputer, alarms and power supply.

Figure 1:
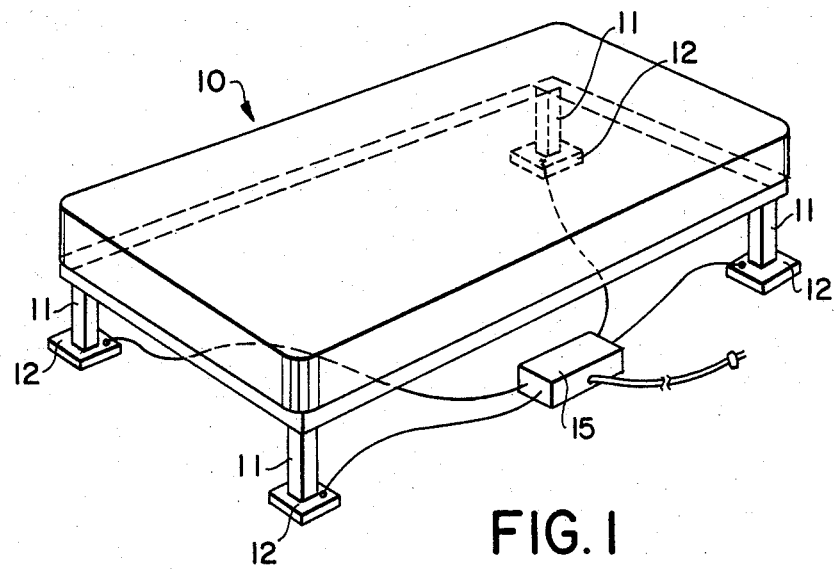
FIG. 1 is a schematic isometric view of a bed with transducers beneath each leg.

Referring to the drawings, in FIG. 1, I have illustrated a bed 10 having legs 11 with sensors 12 attached to the frame beneath each leg. Each sensor 12 is made up of a transducer (which may be a strain gauge type or a piezo electric type transducer) and a low noise fixed gain amplifier.

Figure 2:
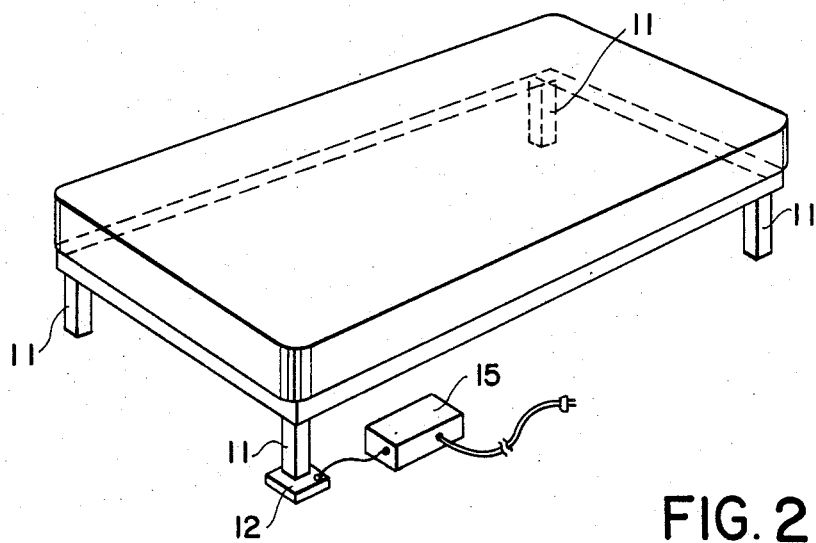
FIG. 2 is a schematic isometric view of a bed with a transducer beneath one leg.

In FIG. 2, I have illustrated bed 10 having legs 11 with a sensor 12 attached to the frame beneath only one of said legs. In such cases it is desirable to adjust the length of the other three legs to maintain the crib in a level state. This can be accomplished in many well known ways, such as by using leveling screws in the legs, etc.

Figure 3C:
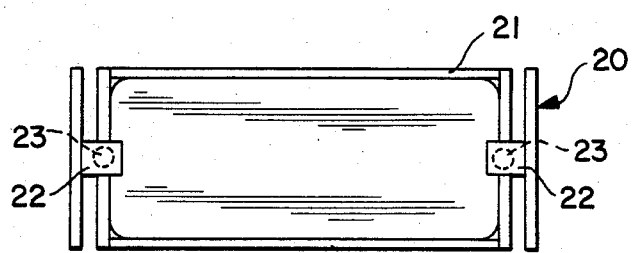
FIGS. 3A, 3B and 3C are schematic side elevation, front elevation and top plan views of a bed with transducer(s) built into the frame of the bed at the hanging support.
Figure 3A:
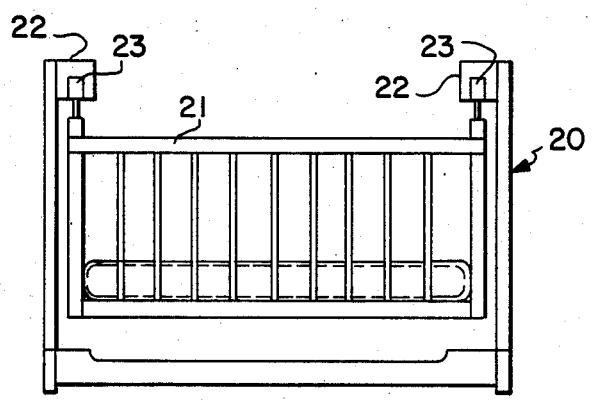
Figure 3B:
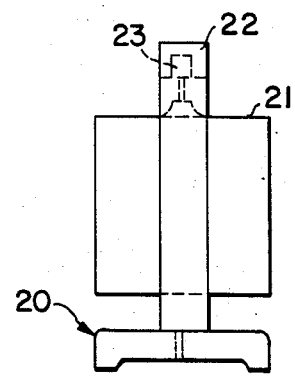

In FIG. 3, I have illustrated a bed 20 having a main crib section 21 that hangs from supports 22. This configuration uses sensor(s) 23 in the support frame. Sensors 23 are of the same type of sensors 12 described above.

Figure 4:
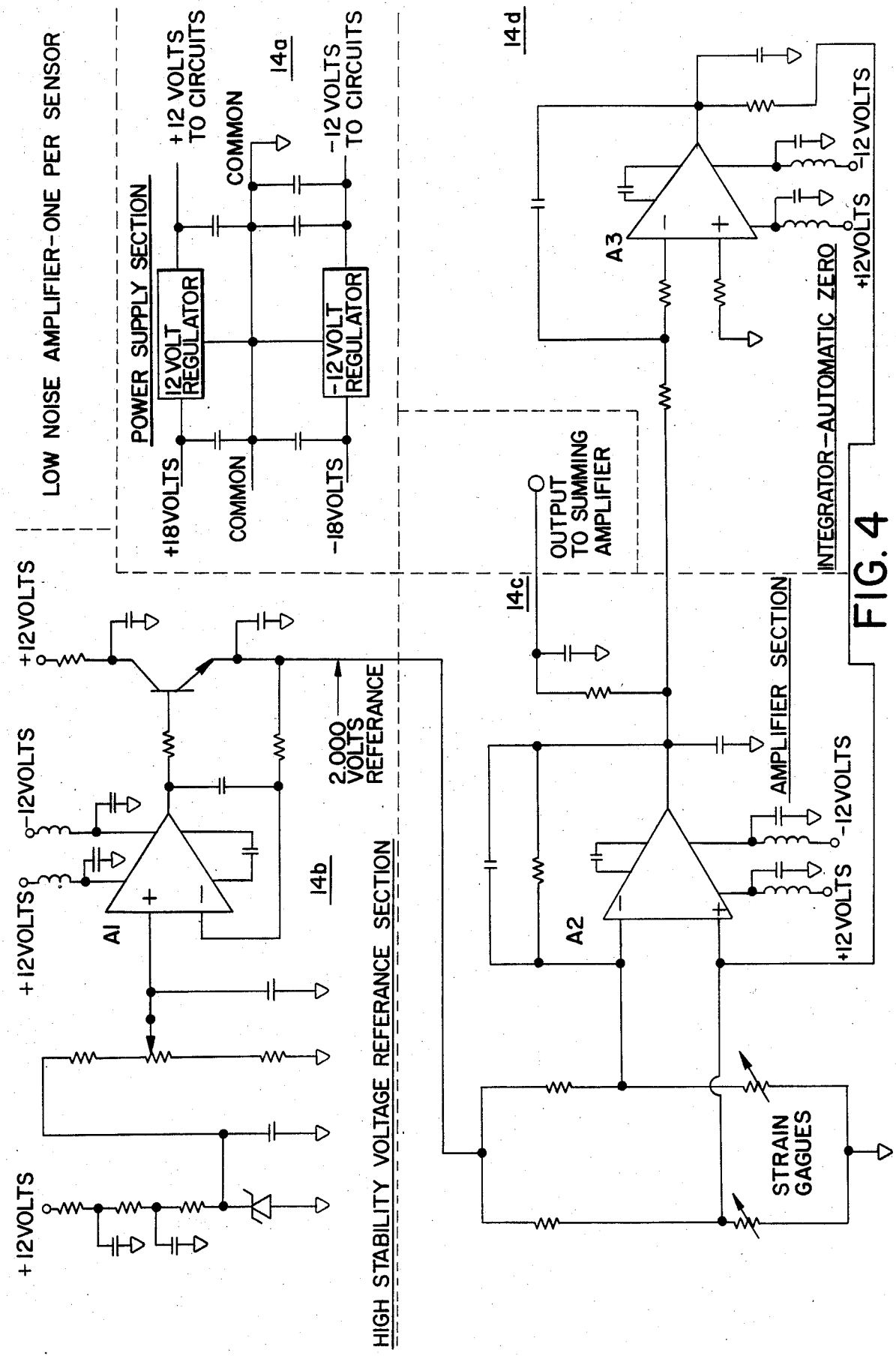
FIG. 4 is a schematic wiring diagram of a present preferred embodiment of a low noise amplifier to be used with each strain gauge sensor.

A low noise fixed gain amplifier which might be used with strain gauge sensor 12 is illustrated in FIG. 4. Such an amplifier preferably has a power section which supplies power to all sections of the amplifier 14a, a high stability voltage reference which supplies a voltage reference to the amplifier bridge section 14b, an amplifier section 14 containing the strain gauges and an integrator section 14d which zeros out the constant weight.

Referring to FIG. 5, the low noise amplifier 14 is connected to a summing amplifier 15 which is in turn connected to a variable gain amplifier 16. The output of the variable gain amplifier goes to the signal level comparator 17. The output of the signal level comparator goes to the microprocessor unit 18. The microprocessor adjusts the variable gain amplifier so a usable signal is sent to the signal level comparator. The microprocessor unit 18 is in turn connected to and energizes one or more alarms 19.

I have found that the sensing of a change in force in the XY horizontal plane at the sensor allows detection of the patient's movements.

In the foregoing specification I have set out certain preferred practices and embodiments of my invention, however it will be understood that it may be otherwise embodied within the scope of the following claims.

I claim:

1. An apparatus for detecting the cessation of force from the acceleration of the mass of the uppermost side of the ribcage from breathing of a human in a crib or bed having a frame for support comprising sensor means on said frame which signals a change in vertical force on said frame as an electrical output signal, amplifier means receiving the electrical output signals from all sensor means and providing an output signal, variable gain means in the amplifier providing matching of the signal with the physical parameters of the patient, microprocessor means comparing successive said signals and providing an output signal if a change occurs and at least one of audible and physical output alarm means receiving the signal from the microprocessor to signal a change in state on the sensor means.

2. An apparatus for detecting the cessation of breathing as claimed in claim 1 wherein each sensor means is a piezo electric transducer coupled with a fixed gain integrating amplifier.

3. An apparatus for detecting the cessation of breathing as claimed in claim 1 wherein each sensor means is a strain gauge transducer coupled with a fixed gain amplifier utilizing integration to zero the amplifier.

4. An apparatus for detecting the cessation of breathing as claimed in one of claims 1 or 2 or 3 wherein each sensor means includes a power source, an amplifier section and an integrator section delivering a final signal to the summary amplifier from each leg.

5. An apparatus for detecting the cessation of breathing as claimed in one of claims 1 or 2 or 3 wherein said sensor means also detects a change of force in a horizontal plane to allow detection of the human.

* * * * *